(12) United States Patent
Amorizzo et al.

(10) Patent No.: US 10,588,657 B2
(45) Date of Patent: Mar. 17, 2020

(54) GUIDING SYSTEM FOR THE INSERTION OF A MEDICAL NEEDLE

(71) Applicants: Ezio Amorizzo, Rome (IT); Andrea Cusano, Caserta (IT); Antonello Cutolo, Naples (IT); Marco Mercieri, Rome (IT); Alberto Micco, Benevento (IT); Armando Ricciardi, Benevento (IT)

(72) Inventors: Ezio Amorizzo, Rome (IT); Andrea Cusano, Caserta (IT); Antonello Cutolo, Naples (IT); Marco Mercieri, Rome (IT); Alberto Micco, Benevento (IT); Armando Ricciardi, Benevento (IT)

( * ) Notice: Subject to any disclaimer, the term of this patent is extended or adjusted under 35 U.S.C. 154(b) by 0 days.

(21) Appl. No.: 15/767,737

(22) PCT Filed: Oct. 17, 2016

(86) PCT No.: PCT/IB2016/056212
§ 371 (c)(1),
(2) Date: Apr. 12, 2018

(87) PCT Pub. No.: WO2017/064682
PCT Pub. Date: Apr. 20, 2017

(65) Prior Publication Data
US 2018/0289390 A1 Oct. 11, 2018

(30) Foreign Application Priority Data

Oct. 16, 2015 (IT) .................. 102015000062613

(51) Int. Cl.
*A61B 17/34* (2006.01)
*A61B 34/20* (2016.01)
(Continued)

(52) U.S. Cl.
CPC .......... *A61B 17/3403* (2013.01); *A61B 5/065* (2013.01); *A61B 17/3401* (2013.01);
(Continued)

(58) Field of Classification Search
CPC ................. A61B 17/34; A61B 34/20
(Continued)

(56) References Cited

U.S. PATENT DOCUMENTS 5,180,365 A * 1/1993 Ensminger ........ A61M 39/0208
604/175
5,356,381 A * 10/1994 Ensminger ........ A61M 39/0208
604/181
(Continued)

FOREIGN PATENT DOCUMENTS

WO WO2012159000 11/2012
WO WO2015023665 2/2015

*Primary Examiner* — Kaveh C Kianni
(74) *Attorney, Agent, or Firm* — Stetina Brunda Garred & Brucker (57) ABSTRACT

A guiding system (1, 101) for guiding the insertion of a needle (2) and a catheter (6) for medical use in a biological tissue, the guiding system (1, 101) comprising: —the needle (2) —the catheter (6) inserted into the needle (2); —an optical fiber (8) provided with at least one optical sensor (10) and inserted into the catheter (6), —a first blocking device (12, 112) for firmly blocking the catheter (6) inside the needle (2).

18 Claims, 8 Drawing Sheets

(51) Int. Cl.
*G02B 6/02* (2006.01)
*A61B 5/06* (2006.01)
*A61B 17/00* (2006.01)
*A61M 25/01* (2006.01)

(52) U.S. Cl.
CPC .......... *A61B 34/20* (2016.02); *G02B 6/02076* (2013.01); *A61B 2017/00022* (2013.01); *A61B 2017/00057* (2013.01); *A61B 2017/3409* (2013.01); *A61B 2034/2061* (2016.02); *A61M 2025/0166* (2013.01)

(58) Field of Classification Search
USPC .......................................................... 385/12
See application file for complete search history.

(56) References Cited

U.S. PATENT DOCUMENTS

| | | | | |
|---|---|---|---|---|
| 5,405,474 | A * | 4/1995 | Berkey | G02B 6/2835 156/250 |
| 5,713,858 | A * | 2/1998 | Heruth | A61M 25/0662 604/175 |
| 6,993,376 | B2 * | 1/2006 | Testardi | A61N 5/1048 250/370.07 |
| 7,189,226 | B2 * | 3/2007 | Auld | A61B 18/22 606/11 |
| 7,848,791 | B2 * | 12/2010 | Schmitt | A61B 5/0066 356/497 |
| 7,854,157 | B2 * | 12/2010 | Kemmochi | C03B 37/0126 72/251 |
| 8,050,523 | B2 | 11/2011 | Younge et al. | |
| 2007/0265503 | A1 * | 11/2007 | Schlesinger | A61B 5/065 600/182 |
| 2008/0009751 | A1 * | 1/2008 | Berndt | A61B 5/0075 600/478 |
| 2008/0249517 | A1 * | 10/2008 | Svanberg | A61N 5/0601 606/15 |
| 2008/0285909 | A1 * | 11/2008 | Younge | A61B 5/1076 385/13 |
| 2009/0099551 | A1 * | 4/2009 | Tung | A61B 5/103 604/530 |
| 2011/0319714 | A1 * | 12/2011 | Roelle | A61B 1/00006 600/118 |
| 2011/0319815 | A1 * | 12/2011 | Roelle | A61B 1/00149 604/95.01 |
| 2011/0319910 | A1 * | 12/2011 | Roelle | A61B 34/71 606/130 |
| 2013/0131499 | A1 * | 5/2013 | Chan | A61B 8/0841 600/424 |
| 2014/0031677 | A1 * | 1/2014 | Iftimia | A61B 5/0066 600/425 |
| 2015/0190123 | A1 * | 7/2015 | Park | A61B 10/0266 600/567 |
| 2016/0256101 | A1 * | 9/2016 | Aharoni | A61B 5/0059 |
| 2018/0289927 | A1 * | 10/2018 | Messerly | A61B 5/0084 |
| 2019/0038228 | A1 * | 2/2019 | Daly | G01K 7/02 |

* cited by examiner

GUIDING SYSTEM FOR THE INSERTION OF A MEDICAL NEEDLE

CROSS REFERENCE TO RELATED APPLICATION(S)

The present application claims priority to PCT International Application No. PCT/IB2016/056212 filed on Oct. 17, 2016, which application claims priority to Italian Patent Application No. 102015000062613 filed Oct. 16, 2015, the entirety of the disclosures of which are expressly incorporated herein by reference.

STATEMENT RE: FEDERALLY SPONSORED RESEARCH/DEVELOPMENT

Not Applicable.

FIELD OF THE INVENTION

The present invention relates to a system for guiding the insertion of a needle for medical use in a biological tissue.

BACKGROUND ART

In clinical practice, there are various tissues or compartments in which a catheter can be inserted by means of a needle for medical use. Among these, for example, the epidural space, one of those most sought for locoregional anesthesia and for the treatment of pain, deserves special attention. Locating the epidural space is currently a subjective method, known as loss of resistance. Such a method is based on the operator's perception of the loss of resistance offered by the piston of a low pressure syringe when the needle-syringe system advances towards the epidural space. In fact, the epidural space is identified by the perception to the touch of the loss of resistance due to the needle passing the yellow ligament, Because of the several false positives, this technique is not particularly accurate and can cause various complications, including accidental dural puncture. Dural puncture causes the leakage of fluid from the dura mater which in turn causes a prolonged and debilitating headache, resulting in longer hospital stay associated with an increase in hospital costs.

In addition to the problem of the needle reaching the epidural space, a large number of epidural anesthesia failures occur because of the wrong positioning or dislocation of the catheter, which take place upon the needle placement. In fact, once the needle has reached the epidural space, or rather once the operator believes to have reached the epidural space, the catheter is manually inserted into the needle and slid therein. The catheter is slid by pushing it with the fingers. In particular, the catheter is slid until it emerges from the needle tip in order to reach the epidural space.

In detail, the wrong positioning may be due to the accidental insertion of the catheter in an intervertebral foramen and sometimes to the exit from the foramen in the paravertebral space. If the catheter ends in the intervertebral foramen, the anesthesia will be incomplete; if it ends in the paravertebral space, the anesthesia will be failed. The intervertebral foramina are lateral to the interlaminar space through which the epidural needle is inserted. Therefore, when the catheter reaches an intervertebral foramen, it undergoes progressive buckling, up to about 90°. In other words, a kinking of the catheter occurs.

The wrong positioning may also be due to the fictitious operator's perception of the location of the epidural space. In this case, by encountering resistance during the advance, the catheter is crushed upon exiting from the needle.

In, addition, the displacement of the catheter may occur due to the catheter traction during the patient's passive or active movement.

The whole operation is particularly complicated also because when the operator believes that the needle has reached the epidural space, he/she must hold the needle locked with one hand and release the syringe with the other hand and take the catheter from the support cart and insert it through the needle into the epidural space. Control with one hand can often result in the loss of the epidural space, and therefore in a failure of the epidural anesthesia.

Document WO2012/159000A2 describes a device which only allows the movement of a catheter inside a needle. To this end, it is provided with free revolving rolls. The device described in this document does not in any way assists the operator in the search for a specific tissue or biological space like the epidural space.

Document US2015/190123A1 describes a catheter comprising a plurality of optical fibers, each provided with a plurality of sensors. This type of catheter is specifically designed for complex applications, in particular for the shape sensing, and therefore requires a complex construction.

Document U.S. Pat. No. 8,050,523B2 also describes a specific catheter, of the steerable type and quite complex.

The need of overcoming the above drawbacks is therefore felt.

SUMMARY OF THE INVENTION

It is an object of the present invention to provide a system which allows to identify biological tissues, spaces and compartments, such as the epidural space, more accurately compared to the prior art. In particular, it is an object of the invention to assist the operator in the insertion of both the needle and the catheter in the desired biological tissue or space.

It is another object of the present invention to provide a system which allows to check the correct positioning of a catheter within a biological tissue, space or compartment.

The present invention achieves these and other objects which will become apparent in the light of the present description, by providing a guiding system for guiding the insertion of a needle and a catheter for medical use in a biological tissue or compartment, the guiding system comprising:

the needle, which is hollow and is provided with an end portion having an edge delimiting an opening of the needle,
said opening having a geometric center,
and said edge comprising a pointed end of the needle;
the catheter inserted into the needle;
an optical fiber provided with at least one optical sensor and inserted into the catheter,
a first locking device for firmly blocking the catheter inside the needle,
wherein the catheter is provided with an end proximal to the pointed end,
wherein the optical fiber is in abutment with the end of the catheter,
wherein the optical sensor is spaced from said end of the catheter by a distance less than or equal to 50 mm,
wherein the position of the catheter with respect to the needle is such that said end of the catheter is between a first position in which the end of the catheter is at the geometric center of the opening of the needle, and a second position in which the end of the catheter is at the pointed end of the needle, whereby any deformations of the catheter are detected by the optical fiber and the optical sensor during the insertion of the needle.

Advantageously, the system of the invention allows the effective identification of a specific biological tissue or compartment, taking advantage of the catheter deformations occurring when inserting the needle and the catheter into the human body, such deformations being detected by the optical sensor.

The first locking device allows to firmly block the catheter in position with respect to the needle. In particular, the first blocking device allows to block the catheter with respect to the needle at a specific position, in order to allow an efficient detection of the deformation of the catheter.

In order to obtain this lock, the first locking device comprises locking means, such as clamping means which clamp the catheter. During the insertion of the needle into the human body, this lock allows the catheter to deform, for example to compress and extend, making the detection by the optical fiber and the respective optical sensor effective. In particular, the sensor is capable of continuous measurements of deformation of the catheter as it crosses and slides through different biological spaces.

Substantially, the insertion of the needle into a specific biological tissue or space is guided by means of the catheter, in particular by means of the optical fiber and the respective optical sensor inserted into the catheter. After checking the placement of the needle in the desired biological tissue, the locking device can release the catheter. The catheter can then be manually slid by the operator, who for example can grab and push the catheter with his/her fingers.

Preferably, but not exclusively, the first locking device also allows a controlled movement of the catheter inside the needle. In this case, preferably, the first locking device comprises both locking means and adjustment means. Preferably, the locking means are distinct from the adjustment means. The adjustment means are adapted to adjust the position of the catheter with respect to the needle. Preferably, but not exclusively, such adjustment means comprise an element adapted to rotate so that a rotation of the element causes a translation of the catheter.

As already mentioned, the system of the invention is particularly adapted to assist and guide the introduction of both the needle and the catheter for medical use in specific human tissues and compartments, in particular the epidural space.

Advantageously, the system of the invention allows to solve the problems related to the placement of the needle and catheter within spaces and compartments in the human body and thus make the placement not only of the needle but also of the catheter in the desired compartment, such as in the epidural space, more effective. In particular, the system of the invention allows measurements in situ and in real time during the insertion of the needle and of the catheter in the human body.

In brief, the system of the invention comprises a catheter which is sensorized by integrating, preferably within its lumen, an optical fiber provided with at least one optical deformation/pressure sensor, preferably of the fiber Bragg grating type, also known as FBG. Alternatively, the fiber with at least one sensor, preferably of the Bragg grating type, can be integrated within the walls of the catheter.

It is particularly advantageous to provide a single optical fiber and integrate a single optical sensor on the optical fiber which is preferably of the Bragg grating type. This solution allows to obtain a relatively simple guiding system which can be manufactured on a large scale in a cost-effective manner. Moreover, this guiding system is associated with a simple and cost-effective optoelectronic interrogation unit which can be for example, of the single channel type.

However, solutions with multiple optical sensors may be provided, of the Bragg grating type or of the Fabry-Perot interferometer type. To the same end, while it is preferred to insert a single optical fiber with the respective optical sensor within the catheter, more than one optical fiber, such as two, and respective optical sensors may be provided within the catheter.

The optical fiber inserted in the catheter is optically connected to an optoelectronic interrogation unit capable of interrogating the optical fiber sensor in real time, processing the reflected signal. Preferably, the interrogation unit is connected to a portable device capable of making the data readily accessible to the operator with the aid of displays, and preferably also of LEDs and acoustic signals. Preferably, a suitable device is also provided for locking the optical fiber in position within the catheter.

The system of the invention finds application, not exclusively, in the field of locoregional anesthesia such as epidural. In this context, the system of the invention is advantageously able to make the location of the epidural space easier by assisting the operator in the insertion of the needle into the epidural space, when the locking device is in the locked configuration. Moreover, when the locking device is in the unlocked position, the system of the invention also allows to verify, during the advance of the sensorized catheter in the epidural space, any undesired placements thereof, like those in the intervertebral foramina, without the aid of imaging methods.

Further advantages of the system of the invention are:
objective method and two-hand control of the needle advancement;
insertion of the sensorized catheter without detachment of the operator's hands from the needle-catheter system;
real-time detection of catheter deformations, so that the anesthesiologist can detect and prevent kinking and retract the catheter up to its straightening, so as to make sure of the correct position of the catheter;
detection of the compression of the catheter on the dural sac, thereby preventing any perforation of the dura mater by the catheter itself;
detection, preferably with alarm, of stretching of the catheter, thereby preventing the exit from the epidural space.

Moreover, as regards the epidural analgesia/anesthesia, the system of the invention allows to reach lumbar, dorsal and cervical levels very far from the point of insertion, being always sure not to cause a transforaminal migration of the catheter. It should be noted that the present invention is not limited to locoregional anesthesia but can find direct application in other contexts and procedures, associated for example with the placement of
endovascular catheters and wires for preventing the wrong positioning in collateral vessels and avoiding the breakage of any thrombi (mostly non-visible in fluoroscopy) which prevent them from advancing;
epidural or peripheral electroneurostimulation catheters: buckling sensing for the placement and stretch sensing for the dislocation.

The present invention also finds application for the lumbar sympathetic block, in particular for preventing the puncture of large-caliber vessels such as the aorta and the inferior vena cava.

According to one aspect, the invention also provides a kit for implementing a guiding system as described above, comprising a catheter, an optical fiber provided with at least one optical sensor; a locking device for blocking the catheter to the needle.

The dependent claims describe preferred embodiments of the invention.

BRIEF DESCRIPTION OF THE FIGURES

Further features and advantages of the invention will appear more clearly from the detailed description of preferred, but not exclusive, embodiments of a guiding system for guiding the insertion of a needle and of a catheter. The description is provided by way of non-limiting example with reference to the accompanying drawings, which are also provided by way of non-limiting example, in which.

The same reference numerals in the figures identify the same elements or components.

DETAILED DESCRIPTION OF PREFERRED EMBODIMENTS OF THE INVENTION

With reference to the Figures, a guiding system or guiding apparatus is shown, for guiding the insertion of a needle 2 and of a catheter 6 for medical use in a biological tissue or compartment, the guiding system comprising:

the needle 2, which is hollow and is provided with an end portion 52 having an edge 51 delimiting an opening 53 of needle 2,
said opening having a geometric center C,
and said edge 51 comprising a pointed end 22 of needle 2;
the catheter 6 inserted into the needle 2;
an optical fiber 8 provided with at least one optical sensor 10 and inserted into the catheter 6,
a first locking device 12, 112 for firmly blocking the catheter 6 inside the needle 2,
wherein catheter 6 is provided with an end 32 proximal to the pointed end 22,
wherein the optical fiber 8 is in abutment with end 32 of catheter 6,
wherein the optical sensor 10 is spaced from said end 32 of catheter 6 by a distance less than or equal to 50 mm,
wherein the position of catheter 6 with respect to needle 2 is such that said end 32 of catheter 6 is between
a first position in which end 32 of catheter 6 is at the geometric center C of the opening of needle 2, and
a second position in which end 32 of catheter 6 is at the pointed end 22 of needle 2,
whereby any deformations of catheter 6 are detected by the optical fiber 8 and the optical sensor 10 during the insertion of needle 2.

In the embodiments shown, there is provided only one optical fiber 8 with only one optical sensor 10, preferably of the optical fiber Bragg grating type.

The system of the invention is therefore provided with one end of catheter 6 emerging from needle 2, so as to transfer the mechanical strains (compressions, expansions and bending) induced by the pressures due to the crossing of the biological tissues to the optical sensor 10 integrated on the optical fiber 8. Since such pressures are closely related with the elastic features of said tissues, the optical fiber 8 provided with the optical sensor 10 is able to provide useful information for a correct placement of needle 2 and catheter 6 within the sought biological space.

Needle 2 is of the medical type, for example of the type used for locoregional anesthesia, preferably for epidural anesthesia. Preferably, this type of needles is not of the steerable type. In particular, it is neither of the steerable type nor in manual or robotized manner.

Figure 7A:
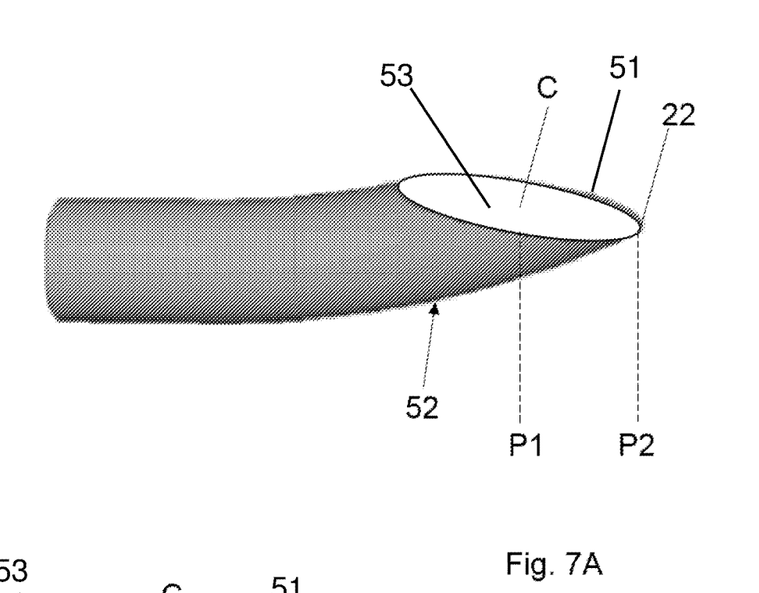
FIG. 7a schematically shows a portion of a type of needle.
Figure 7B:
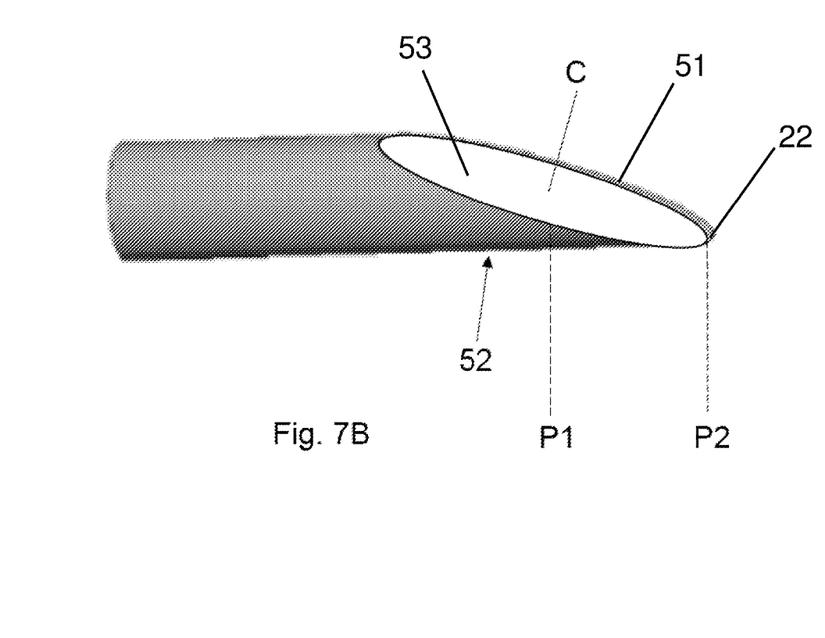
FIG. 7b schematically shows a portion of another type of needle.

Needle 2 is provided with a lumen, being internally hollow. Needle 2 is substantially cylindrical and has an end portion 52, preferably curved, which comprises an edge 51 delimiting an opening 53. Opening 53 has a geometrical center C. Edge 51 comprises a pointed end 22, or tip 22, which is the tip of needle 2. The pointed end 22 is substantially the portion at the maximum distance from base 24 of needle 2. The end portion 52 is cut obliquely with respect to the longitudinal axis of needle 2, with a cutting angle other than 90°. FIGS. 7a and 7b show two examples of needles which can be used in the present invention, respectively, in particular a portion of such needles.

The position of catheter 6 with respect to the needle is such that the closed end 32 of catheter 6 is between a first position P1, in which end 32 of catheter 6 is at, or aligned with, the geometric center C of the opening of needle 2, and a second position P2, in which end 32 of catheter 6 is at, or aligned with, the pointed end 22 of needle 2.

Typically, edge 51, or contour, is elliptical. The first position P1 is at, or aligned with, center C of such an ellipse; the second position P2 is at, or aligned with, the end of the major axis of the ellipse, which corresponds to tip 22 of the needle.

This ensures a physical contact of catheter 6 with the biological tissues during the insertion of needle 2 in the human body.

A base 24 is provided at the other end of needle 2, opposite to tip 22, from which two lugs 26 branch off which form a single piece and which extend perpendicularly to the longitudinal axis of needle 2. Base 24 also comprises a fitting 28 of the luer type, and in particular of the female luer type. As is known, luer connectors are a standard of the fitting systems used to connect together components for medical use and typically consist of a barrel (female luer) made for example of transparent polypropylene (the color of which allows to identify the diameter of the needle) which locks by means of the connection to the plastic cone (male luer) of syringes. Other liter connection systems are referred to as luer lock, in which the female luer connector is screwed to the male luer connector.

Catheter 6 is internally hollow and has an end portion 72, with a closed and preferably rounded end 32. Moreover, the end portion is provided with one or more lateral holes 5 which allow the release of a drug.

The optical fiber 8 is inserted within catheter 6 up to abutment with the closed end 32 of catheter 6. Preferably, in order to improve the mechanical properties thereof, the optical fiber 8 is coated around the cladding with polyamide or other biocompatible material suitable for clinical use.

The outer diameter of the optical fiber 8, including any coating, is smaller than the inner diameter of the lumen of catheter 6 so that the optical fiber 8 itself can be easily inserted/removed in/from catheter 6. An optical connector 20 is provided at the other end of the optical fiber 8, that is, opposite to that in abutment with catheter 6, for connecting the optical fiber 8 to the optoelectronic interrogation unit (not shown).

At least one optical sensor 10, preferably one sensor of the Bragg grating type, is integrated along the axis of the optical fiber 8, at a certain distance from the end adapted to abut with catheter 6, which acts as a deformation/pressure sensor. A brief description of the Bragg grating is given in the following description. The distance between the optical sensor 10 and the end 32 of catheter 6, or the distance between the end of the optical fiber 8 adapted to abut with end 32 of catheter 6, is less than or equal to 50 mm. Preferably, such a distance is of between 10 and 50 mm, more preferably between 10 and 30 mm, even more preferably between 10 and 20 mm, for example of about 15 mm. These distances allow an effective detection by the optical sensor 10.

The optical fiber 8 is fixed in position within catheter 6 by a locking device 34. The blocking device 34 is preferably mounted in the vicinity of the end (opposite with respect to tip 22 of needle 2) of catheter 6 from which the optical fiber 8 ending with the optical connector 20 emerges. By way of example, the locking device 34 is a cable clamp, comprising a base 35 in which a groove is formed for accommodating catheter 6 with the optical fiber 8 therein. A closing lever 36 is pivoted to base 35 which, when placed in a horizontal position with respect to base 35, locks the optical fiber 8 to catheter 6 by means of a compression.

Catheter 6 with the optical fiber 8 with optical sensor 10 therein is arranged inside needle 2. For descriptive purposes, the assembly formed by catheter 6 with the optical fiber 8 with the optical sensor 10 therein, in particular with Bragg grating, is also referred to as sensorized catheter 6. The inner diameter of the lumen of needle 2 is larger than the outer diameter of catheter 6 in order to make the insertion and removal thereof easy.

The sensorized catheter 6 is inserted into needle 2 and blocked in a specific position, defined above, by means of a suitable locking device 12, 112 connected to needle 2. In general, the locking device can be connected to a common medical needle 2, preferably by means of a luer connection;

keeps the sensorized catheter 6 blocked during the penetration of needle 2;

allows the sensorized catheter 6 to slide inside needle 2 when the penetration interrupted.

Advantageously, the locking device according to the invention is also compact and lightweight, so as to be easy to handle.

Exemplary and non-exclusive embodiments of locking devices are described hereinafter.

Figure 1:
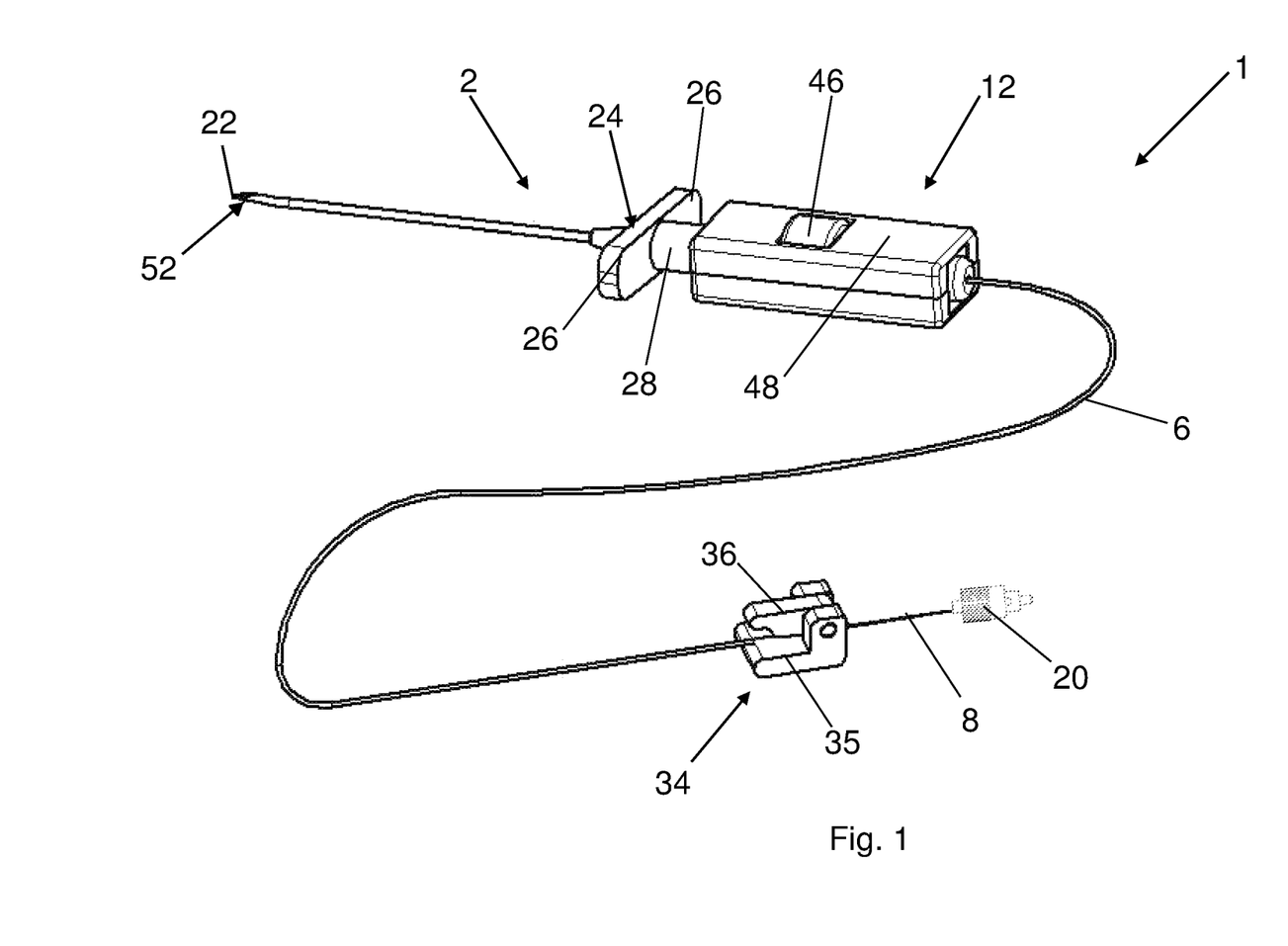
FIG. 1 shows a system according to a first embodiment of the invention.
Figure 2:
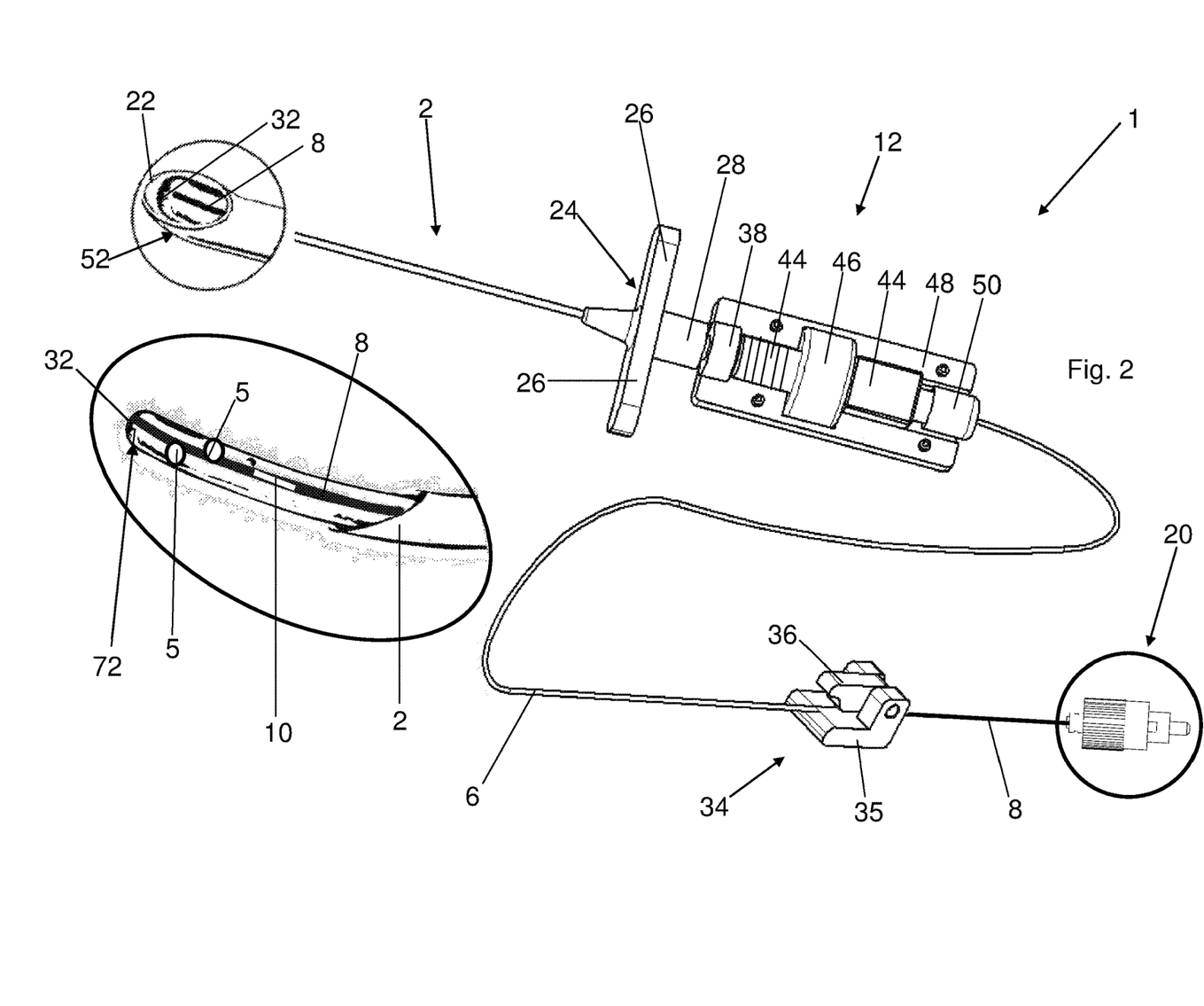
FIG. 2 shows the system in FIG. 1, in which some enlarged details are shown, with parts in transparency, and in which a component is partially disassembled.
Figure 3A:
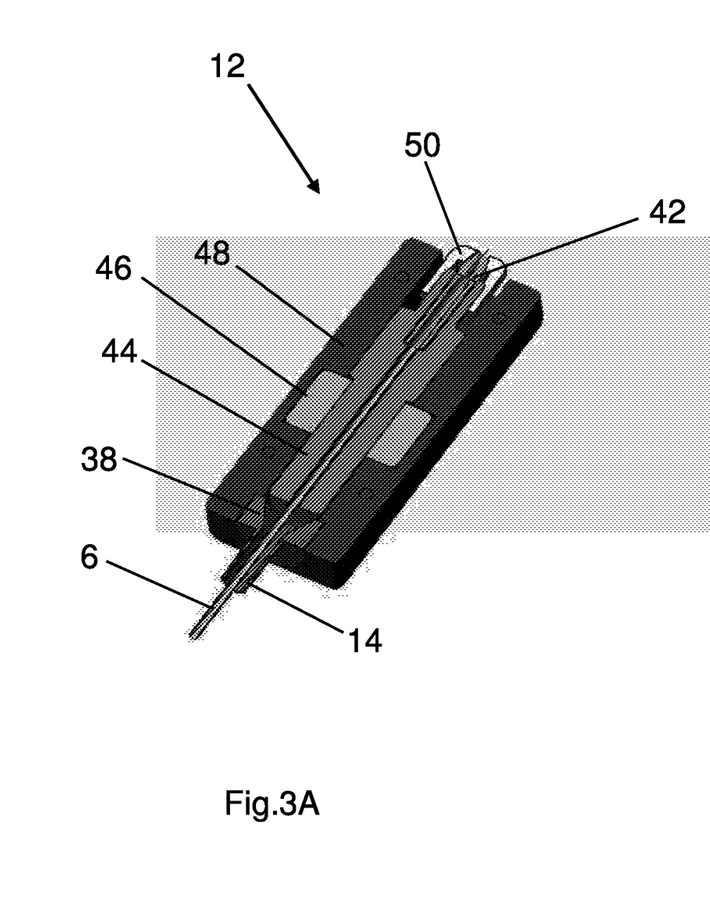
FIG. 3a shows a section of a component of the system in FIG. 1.
Figure 3B:
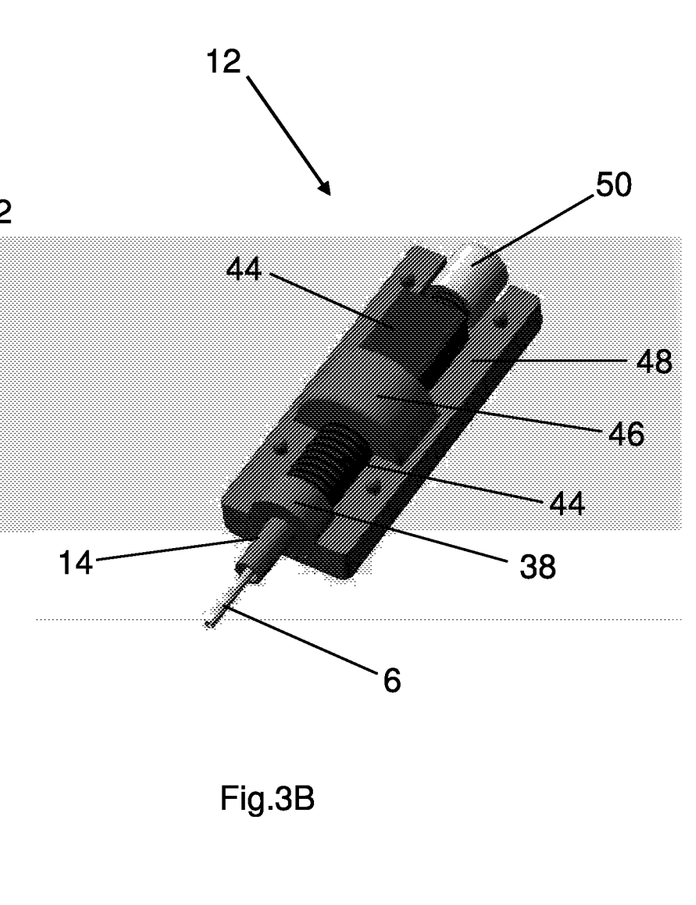
FIG. 3b shows some parts of a component of the system in FIG. 1.

According to a first embodiment (FIG. 1-3), the locking device 12 also allows a controlled movement of catheter 6 only when the operator actuates the moving means. In particular, locking means distinct from the moving means are provided. In order to allow the movement of catheter 6, a force must act on catheter 6, provided by the actuation of the moving means, which must be greater than the locking force of the locking means. The locking device 12 is configured so that such a force is greater than the forces to which catheter 6 is subject during the insertion of needle 2.

The locking device 12 allows the fine sliding of catheter 6 and has a stroke of a few centimeters, for example but not exclusively ranging from 1 to 5 cm.

The locking device 12 comprises: an inlet block 38 with a fitting region 14, preferably a male liter fitting, a clamp gripper 42, a screw 44 arranged within a nut screw 46, a bolt 50 and a seat 48 for such components, provided with an opening from which the nut screw 46 projects partially. Screw 44 comprises a parallelepiped-shaped portion arranged between two externally threaded cylindrical portions. Moreover, screw 44 is provided with a central channel in which the sensorized catheter 6 is inserted, which runs through the locking device 12 from side to side. By means of the male luer fitting 14, of the interlocking or screwing type, the locking device 12 can easily be connected to needle 2 and in general to any standard medical needle.

The inlet block 38 substantially serves to integrate, or mount, the locking device 12 with needle 2.

Once constrained to needle 2, for example by insertion of fitting 28 in, or on, the fitting region 14, and once the sensorized catheter 6 has been inserted in the locking device 12, the latter is able to both block the sensorized catheter 6 in position with respect to needle 2, during the insertion of the needle, and to allow it to slide in both directions, once the needle has reached the desired biological tissue.

Locking means are used to block the sensorized catheter 6, in particular the clamp gripper 42 capable of clamping, thereby constraining the sensorized catheter 6. The position of the sensorized catheter 6 is blocked due to the clamp gripper 42. In particular, an advance of the sensorized catheter 6 is not allowed without the rotation of the nut screw 46. In fact, a force is required, provided by the rotation of the nut screw 46, which must be greater than the clamping force of the clamp gripper 42 to translate the sensorized catheter 6 in a controlled manner.

Gripper 42 is integrated in screw 44, on which a bolt 50 is in turn screwed. When by screwing, bolt 50 reaches the stroke end, it clamps the end part of the clamp gripper 42 up to close it so as to keep the sensorized catheter 6 blocked, so that it can move integrally with screw 44.

The sliding of the sensorized catheter 6 is achieved by means of screw 44 and the nut screw 46. This system is able to transform a rotary motion into a translation motion by means of a helical coupling obtained so that the rotation of one of the two elements (prevented from translating) causes the translation of the other (prevented from rotating). In the specific case, blocking the translation of the nut screw 46 and rotating the nut screw 46 causes a translation of screw 44.

Constraining the sensorized catheter 6 to screw 44 by means of the clamp gripper 42, thereby locking the translation of screw 44, and rotating the nut screw 46, causes the translation of the sensorized catheter 6. The translation of the nut screw 46 is locked since it projects partially with respect to the opening of seat 48.

A recess is formed on the inner wall of the seat in which both the nut screw 46 and screw 44 are inserted. Therefore, by constraining screw 44 to seat 48 by interlocking, for example by means of the parallelepiped-shaped portion, screw 44 cannot rotate and the rotation of the nut screw 46 will cause translation of screw 44. The sensorized catheter 6 then translates together with screw 44, being constrained thereto by means of the clamp gripper 42. Each complete rotation of the nut screw 46 causes a translation of a few centimeters, for example but not exclusively ranging from 1 to 5 cm, of screw 44 and thereby of the sensorized catheter 6. By way of example only, seat 48 may be rectangular or cylindrical in shape.

Figure 4:
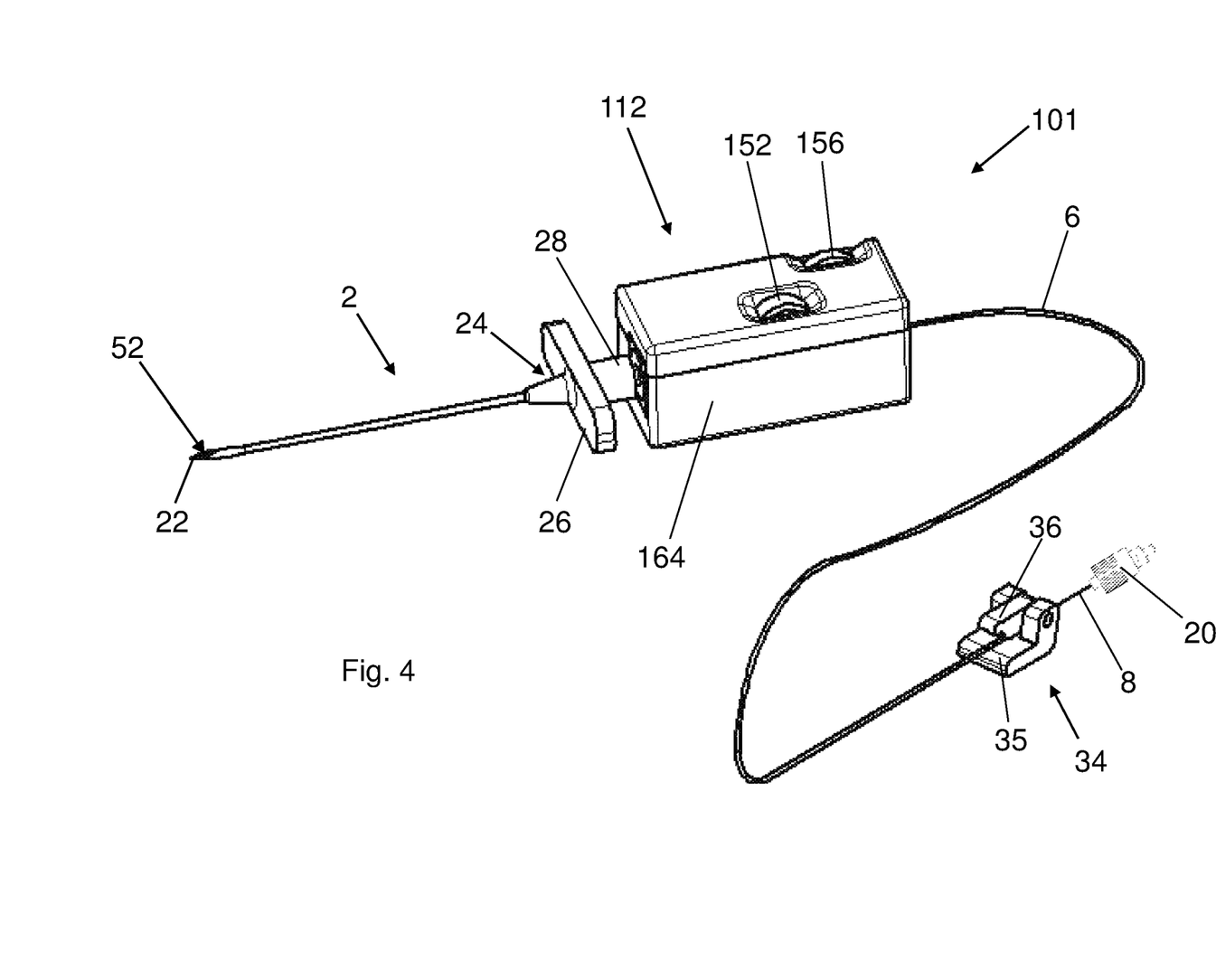
FIG. 4 shows a system according to a second embodiment of the invention.
Figure 5:
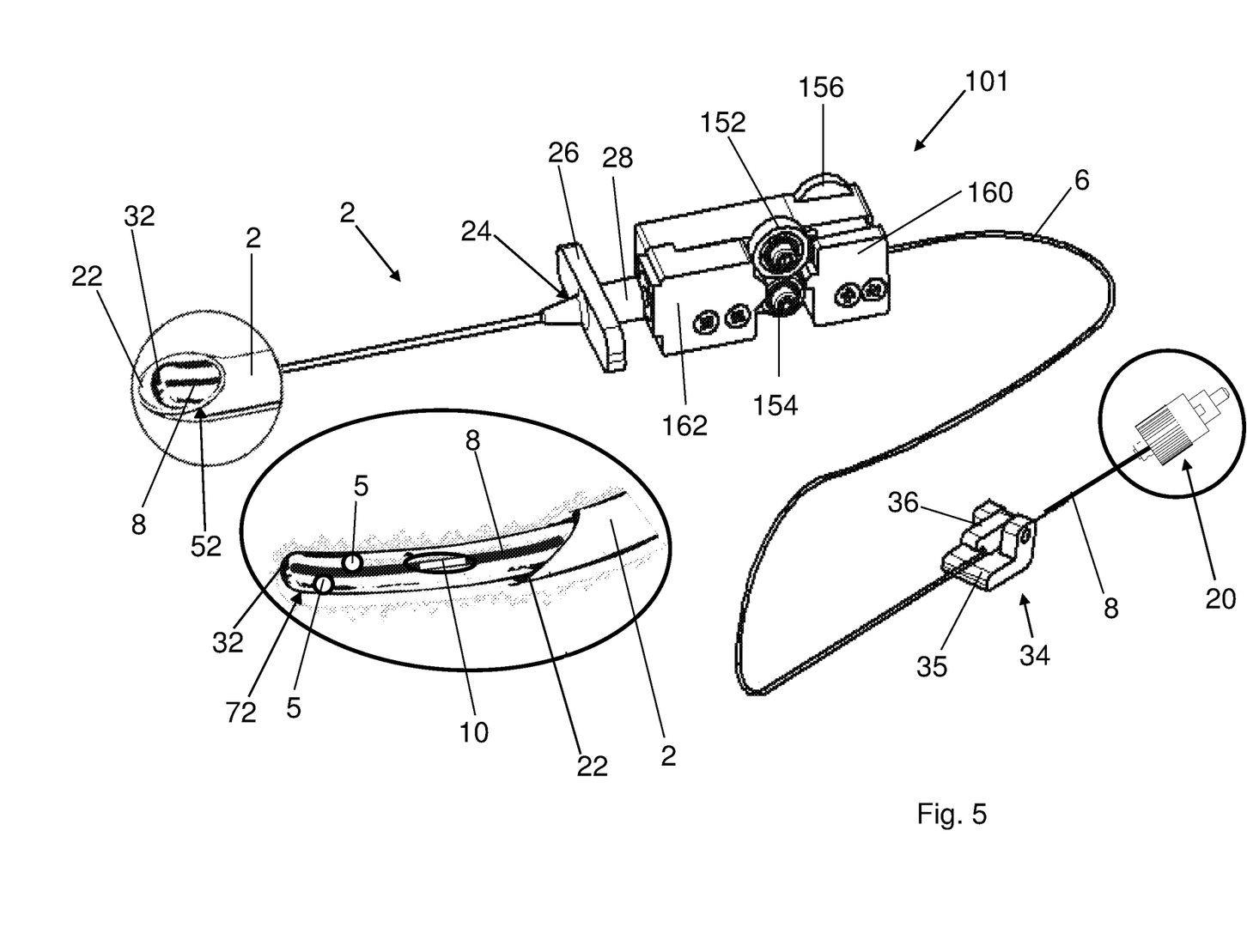
FIG. 5 shows the system in FIG. 4, in which some enlarged details are shown, with parts in transparency, and in which a component is partially disassembled.
Figure 6A:
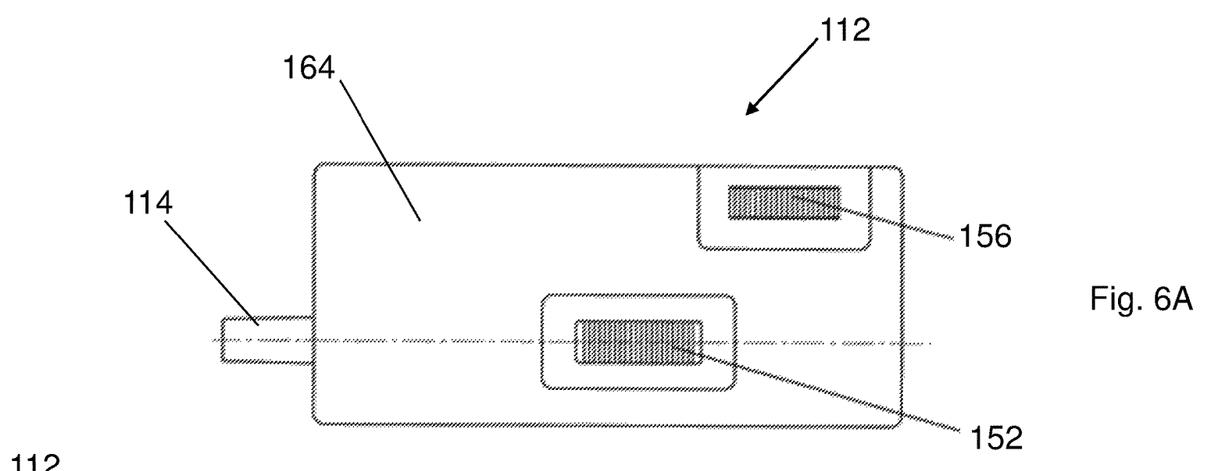
FIG. 6a shows a top view of one side of the component of the system in FIG. 4.
Figure 6B:
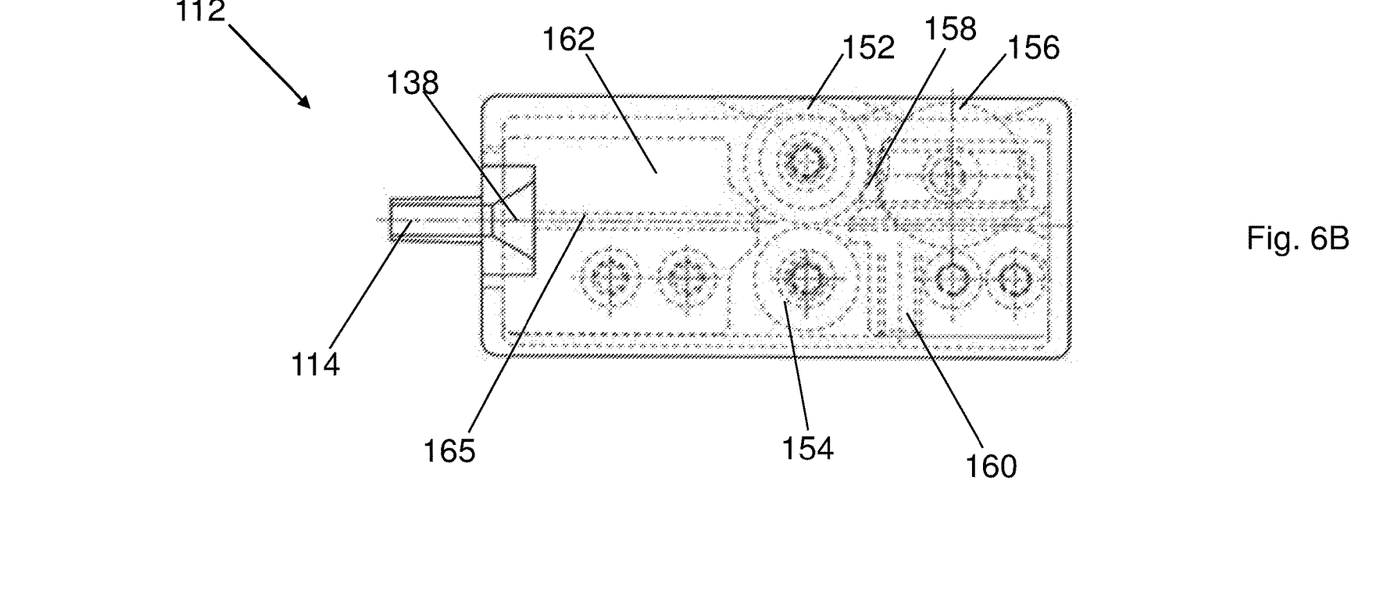
FIG. 6b shows a top view of another side of a component in FIG. 4, in which a part is shown in transparency.

In a second embodiment (FIG. 4-6), the locking device 112 also allows a controlled movement of catheter 6 only when the operator actuates the moving means. In particular, locking means distinct from the moving means are provided. The locking means act on the moving means so as to allow or prevent the actuation thereof by the operator. In order to lock and unlock the moving means, the locking means switch from a locking position to an unlocking position. When the locking means lock the actuation of the moving means, catheter 6 is firmly locked in position. In order to allow the movement of catheter 6, the moving means must be unlocked.

Once the moving means have been unlocked, preferably, the locking device 112 allows a controlled and unlimited stroke of the sensorized catheter 6. The locking device 112 comprises:

a seat 164 provided with two openings; an inlet block 138 with a fitting region 114, preferably a male liter fitting; two advance rollers 152, 154, of which one advance roller 152 provides an advance control dial and partially protrudes from one of the openings of seat 164; a rotary control locking ring nut 156 which partially protrudes from seat 164; locking means, comprising brake 158, for locking the advance roller 152 into position, the locking ring nut 156, which controls brake 158; and two elements, or alignment blocks 160, 162.

As for the locking device 12 described above, the inlet block 138 has the function of allowing the integration of the blocking/sliding device 112 with needle 2. The sensorized catheter 6 is placed between the two advance rollers 152, 154, for example consisting of ball bearings or bushings, slightly subject to pressure, so that by rotating the advance roller 152, the sensorized catheter 6 may move forward or backward inside the needle according to the rotation direction. The alignment elements 160, 162, arranged on the left and on the right, respectively, of the advance rollers 152, 154 are intended to allow the placement of the sensorized catheter 6 inside the locking device, thereby aiding the insertion of the sensorized catheter 6 at the inlet, and aiding the exit of needle 2 towards the lumen at the outlet. The alignment elements 160, 162 are provided with a hole 165 inside which the sensorized catheter 6 passes. Hole 165 has a diameter slightly larger than that of the sensorized catheter 6 so as to allow it to slide.

The advancement of the sensorized catheter 6 can be blocked by the locking ring nut 156, the rotation axis of which is decentralized. Therefore, a rotation of the locking ring nut 156 allows the latter to intercept or not intercept brake 158, which presses against the advance roller 152 so as to lock the rotation thereof. The advance roller 152 and the locking ring nut 156 slightly protrude from seat 164 so that they can be operated and thus rotated from the outside with the fingers. The locking ring nut 156 has the function of keeping the two advance rollers 152, 154 blocked or, if it is unlocked, of allowing the rotations of the advance rollers. In other words, in the operation of the system of the invention, during the insertion of needle 2, the locking ring nut 156 is active, i.e. the advance rollers are blocked, and the sensorized catheter 6 does not move with respect to needle 2. When the needle is stationary, i.e. once the insertion of needle 2 has ended, in order to facilitate the advance of the sensorized catheter 6, the locking ring nut 6 is deactivated by rotating it by 180°, so that the advance rollers 152, 154 are free to rotate, thereby allowing the advance of the sensorized catheter 6.

The locking devices 12, 112 are preferably made of polycarbonate a thermoplastic polymer widely used in the medical field as it can be effectively sterilized in autoclave or by gamma radiation.

Both locking devices 12, 112 are intended to keep the sensorized catheter 6 constrained, for example at a point, while a force is applied on the end due to the pressure exerted by the biological tissues crossed during the insertion of needle 2. In fact, the resistance of the tissues in contact with the sensorized catheter 6, particularly with end 32 during the advance step thereof, is directly proportional to the strain undergone by the optical fiber Bragg grating placed inside the catheter;

allow the sensorized catheter 6 to exit from the tip of needle 2 in a controlled and measurable manner so as to slide it inside the human body for carrying out measurements of deformation and bucking in situ using the optical fiber sensor (i.e. the Bragg grating).

In general, when a blocking and moving device is used, it is preferably provided with indication means, such as a graduated scale, which allow the position of the catheter to be indicated, in particular which allow the advancement extent of the catheter with respect to the needle tip to be indicated.

According to an embodiment (not disclosed), a locking device is provided which is configured exclusively for locking, by means of locking means, the position of the sensorized catheter up to reaching the desired biological tissue, and for unlocking the catheter once such a tissue has been reached.

This locking device has a luer fitting for constraining the needle, and catheter completely crosses the locking device. Preferably, a groove or a channel is provided where the catheter is accommodated. Locking means are provided, such as a button, which can be activated by the operator. The locking means are configured to act on the catheter so as to lock the position thereof. Preferably, a mechanism is provided which keeps the locking means in the locked position and which allows the catheter to be unlocked.

The description of the above locking devices should not be deemed as limiting. In fact, other locking or locking and moving devices may also be used without departing from the scope of the present invention.

After providing an exemplary description of the system according to the invention, an example of the operation thereof is now provided with reference to the execution of an epidural anesthesia.

In this case, pressure is an important parameter of differentiation. Indeed, the loss of resistance technique, which is the most common procedure currently used, is based on the perception of density variation between the yellow ligament and the epidural space. In particular, the continuous pressure monitoring according to the invention allows to achieve a high specificity and sensitivity in the identification of the epidural space. In addition to locating the epidural space and thereby properly placing the needle, the system 1, 101 of the invention also allows to monitor any wrong positioning of catheter 6 in the epidural space. In fact, during the sliding and placement of catheter 6 in the epidural space, thanks to the optical fiber 8 provided with optical sensor 10, which moves integrally with catheter 6, any deformations due to the bending of catheter 6 itself can be detected, which are associated with kinking phenomena, i.e. when catheter 6 fits within spaces involving high bending radii of the catheter itself. Therefore, the system of the invention allows not only to locate the epidural space during the advance of needle 2, but also to monitor the proper placement of catheter 6 in the epidural space, preventing catheter 6 itself from ending into intervertebral foramina, thereby causing the failure of the epidural anesthesia.

As already described above, in the system of the invention, catheter 6 is sensorized by the insertion of an optical fiber 8 in the lumen thereof, including at least one optical sensor 10, preferably one Bragg grating.

Figure 8:
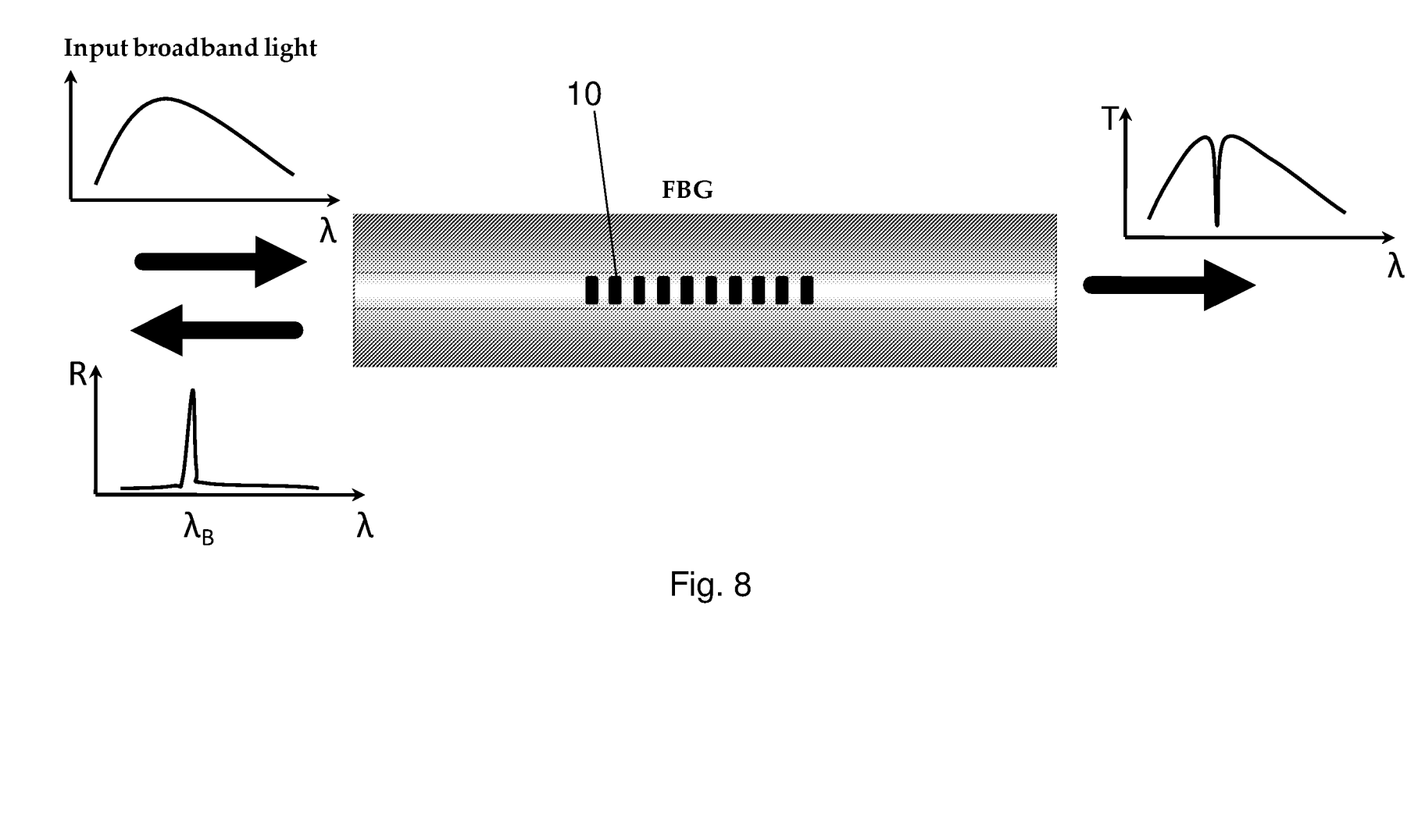
FIG. 8 schematically shows the operation of a sensor used in the system of the invention.

The Bragg grating, also known as "Fiber Bragg Grating" (FBG), can be easily manufactured and integrated within the optical fiber using a UV lithographic process. With particular reference to FIG. 8, the FBG is an optical fiber segment characterized by a periodic modulation of the refractive index along the axis of the fiber core. Such a grating behaves like a band-pass filter in reflection and a band-stop filter in transmission. The reflection peak is centered at the Bragg wavelength given by $\lambda_B = 2 n_{eff} \Lambda$ where $n_{eff}$ is the effective refraction index of the medium, $\Lambda$ is the grating period. Since a longitudinal deformation, or strain, modulates both n and $\Lambda$, the Bragg wavelength undergoes a shift following a perturbation of the environment outside the fiber. Therefore, in the system of the invention, as the sensorized catheter 6 is inserted into the human body, the optical sensor 10 undergoes a stretching or a buckling depending on the elasticity of the tissues which are crossed. The compressions and expansions of the optical sensor 10, i.e. of the FBG, involve a shift of the Bragg wavelength towards shorter or longer wavelengths, respectively. When the sensorized catheter 6 and thus the FBG bend (in particular for bending radii for which the condition of light confinement is no longer satisfied by total internal reflection), in addition to a shift of the Bragg wavelength, there is also a strong reduction in the intensity of the reflected peak due to light escaping from the fiber core and therefore to propagation losses. This phenomenon allows to monitor any kinking of the catheter during the steps of placing it in the biological spaces.

The interrogation of the optical sensor 10 takes place through an optoelectronic interrogation unit directly connected to the optical fiber Bragg grating by means of the optical connector 20.

It is preferred that the interrogation units substantially comprises a light source, a spectrophotometer which measures the optical signal reflected by the FBG, and an directional optical fiber coupler for the interrogation in reflection of the optical sensor 10. The interrogation unit then processes the collected data, monitors the temporal variations of the spectrum reflected by the Bragg grating (such as a shift in the wavelength and intensity variations associated with the reflected peak), and associates them with pressure measurements. In practice, the interrogation unit contains all the devices and electronic components capable of processing the data acquired. The data acquired and in particular the trends in real time of the intensity and wavelength of the reflected Bragg peak are sent to data processing means adapted to process and display said data. For example, a device may be provided such as a PC, tablet, etc., the display of which displays information which can be read in real time by the operator.

The system as a whole works as follows: the optical fiber 8 with optical sensor 10 is optically connected by means of an optical connector 20 to the interrogation unit. A light signal generated by the source is coupled to the optical fiber 8 incorporated into catheter 6 in turn inserted into needle 2 and travels therein, thus reaching the Bragg grating optical sensor 10. The Bragg grating reflects a light share at a specific wavelength which goes back to the interrogation unit through the same fiber. Therefore, when needle 2 and the sensorized catheter 6 inserted therein cross different types of tissues, the optical sensor 10 detects and transmits an optical signal to the interrogation unit related to the pressure changes to which it is subject. In fact, the optical fiber sensor 10 is designed so that any specific variation of its geometric and physical properties (for example due to strain and buckling) matches a change of the reflected light signal. The interrogation unit includes a detection module capable of measuring the spectrum reflected by the sensor and processing the data acquired, possibly by correlating the spectral changes to pressure changes. By monitoring these changes, the system is therefore able to provide information about the position of needle 2 when passing from one tissue to another, and about the number of tissues crossed during the insertion, bends of the catheter, etc.

The system of the invention allows to place the needle and thus the sensorized catheter 6 in the biological space of interest. The system of the invention is connected to the optoelectronic interrogation unit by means of the optical connector 20. The operator, such as the physician, inserts needle 2 into the patient's body by preferably applying a continuous pressure on needle 2, and then on the sensorized catheter 6 which is constrained thereto by means of the locking device, thus favoring the penetration of needle 2 through the various tissues. Depending on the composition (in terms of density, elasticity, etc.) of the tissues crossed, the FBG optical fiber sensor 10 integrated into catheter 6 undergoes different compressions which directly convert into variations of the reflected optical signal. These variations are measured by the interrogation unit to which the sensorized catheter 6 is constrained and displayed on the device display (PC, tablet, etc.) which interfaces with the interrogation unit. When the operator sees a combination of measured parameters (such as sudden variations in the reflection peak wavelength) compatible with a relaxation of catheter 6 inside the human body, shown on the display, he/she will stop the penetration and will check that the sought space has been reached, possibly using the sliding system. In fact, at this point, the sensorized catheter 6 can be slid into needle 2 and inserted in the biological spaces, checking the correct placement (thus avoiding kinking phenomena of the catheter) by monitoring the stability of the optical signal reflected on the display (in terms of wavelength and/or reflection peak intensity). Finally, once catheter 6 has been properly placed, the optical fiber 8 can be extracted from catheter 6 by acting on device 34, so as to allow the administration of any drugs.

Alternatively, if the physician deems it necessary, the catheter may be extracted from the needle and a drug may be directly administered through the needle.

The invention claimed is:

1. A guiding system for guiding the insertion of a needle and a catheter for medical use in a biological tissue or compartment, the guiding system comprising:

the needle, which is hollow and is provided with an end portion having an edge delimiting an opening of the needle,
said opening having a geometric center,
and said edge comprising a pointed end of the needle;
the catheter inserted into the needle;
an optical fiber provided with at least one optical sensor and inserted into the catheter,
a first locking device for firmly blocking the catheter inside the needle,
wherein the catheter is provided with an end proximal to the pointed end,
wherein the optical fiber is in abutment with said end of the catheter,
wherein the optical sensor is spaced from said end of the catheter by a distance less than or equal to 50 mm,
wherein the position of the catheter with respect to the needle is such that said end of the catheter is between
a first position in which the end of the catheter is at the geometric center of the opening of the needle, and
a second position in which the end of the catheter is at the pointed end of the needle,
whereby any deformations of the catheter are detected by the optical fiber and the optical sensor during the insertion of the needle, and wherein the first locking device comprises locking means for locking the catheter, and adjustment means adapted to adjust the position of the catheter in a controlled manner with respect the needle, said adjustment means being distinct from the locking means.

2. The system according to claim 1, comprising only one optical fiber.

3. The system according to claim 2, wherein the optical fiber is provided with only one optical sensor.

4. The system according to claim 1, wherein the optical sensor is spaced from said end of the catheter by a distance of between 10 and 50 mm.

5. The system according to claim 4, wherein the optical sensor is spaced from said end of the catheter by a distance of between 10 and 30 mm, preferably between 10 and 20 mm.

6. The system according to claim 1, wherein the optical sensor has an axial length of between 1 and 15 mm, and wherein the longitudinal axis of the optical sensor is parallel to the longitudinal axis of the optical fiber.

7. The system according to claim 1, wherein the needle is for locoregional anesthesia, particularly for epidural anesthesia.

8. The system according to claim 1, wherein said end of the catheter is closed and wherein said end portion of the catheter is provided with at least one lateral opening.

9. The system according to claim 1, wherein said locking means are configured to act directly on the catheter to lock it in position, or wherein said locking means are configured to act on the adjustment means to lock the catheter in position.

10. The system according to claim 9, wherein said adjustment means comprise an element adapted to rotate so that a rotation thereof causes a translation of the catheter.

11. The system according to claim 1, comprising a second locking device adapted to lock the optical fiber in place inside the catheter.

12. The system according to claim 1, comprising an optoelectronic interrogation unit adapted to be connected to the optical fiber by means of a connector to receive data from said optical sensor.

13. The system according to claim 12, wherein there are provided data processing means adapted to process and display said data.

14. A kit for assembling a system according to claim 1, comprising said needle, said catheter, and said optical fiber provided with said sensor.

15. A guiding system for guiding the insertion of a needle and a catheter for medical use in a biological tissue or compartment, the guiding system comprising:
the needle, which is hollow and is provided with an end portion having an edge delimiting an opening of the needle,
said opening having a geometric center,
and said edge comprising a pointed end of the needle;
the catheter inserted into the needle;
an optical fiber provided with at least one optical sensor and inserted into the catheter,
a first locking device for firmly blocking the catheter inside the needle,
wherein the catheter is provided with an end proximal to the pointed end,
wherein the optical fiber is in abutment with said end of the catheter,
wherein the optical sensor is spaced from said end of the catheter by a distance less than or equal to 50 mm,
whereby any deformations of the catheter are detected by the optical fiber and the optical sensor during the insertion of the needle and wherein the first locking device comprises locking means for locking the catheter, and adjustment means adapted to adjust the position of the catheter in a controlled manner with respect the needle, said adjustment means being distinct from the locking means.

16. The system according to claim 15, wherein said locking means are configured to act directly on the catheter to lock it in position, or wherein said blocking means are configured to act on the adjustment means to lock the catheter in position.

17. The system according to claim 15, wherein said adjustment means comprise an element adapted to rotate so that a rotation thereof causes a translation of the catheter.

18. The system according to claim 15, comprising a second locking device adapted to lock the optical fiber in place inside the catheter.

* * * * *